United States Patent [19]

Higgins et al.

[11] Patent Number: 5,275,597
[45] Date of Patent: Jan. 4, 1994

[54] PERCUTANEOUS TRANSLUMINAL CATHETER AND TRANSMITTER THEREFOR

[75] Inventors: Sheryl W. Higgins, Silverado; Jim-Son Chou, Irvine; Hal Heitzmann, Irvine; Jeffery S. Dove, Irvine; Lauralan Grisoni, Aliso Viejo, all of Calif.

[73] Assignee: Baxter International Inc., Deerfield, Ill.

[21] Appl. No.: 883,986

[22] Filed: May 18, 1992

[51] Int. Cl.⁵ .......................................... A61N 5/02
[52] U.S. Cl. ................................. 606/33; 607/154; 607/116
[58] Field of Search ............... 128/789, 786, 787, 788, 128/804; 606/27, 28, 29, 33, 40, 39

[56] References Cited

U.S. PATENT DOCUMENTS

| | | | |
|---|---|---|---|
| 4,154,246 | 5/1979 | LeVeen | 128/804 X |
| 4,601,296 | 7/1986 | Yerushalmi | 128/804 |
| 4,681,122 | 7/1987 | Winters et al. | 128/804 X |
| 4,813,429 | 3/1989 | Eshel et al. | 128/804 X |
| 4,945,912 | 8/1990 | Langberg | 606/33 X |
| 4,993,430 | 2/1991 | Shimoyama et al. | 128/784 |
| 5,057,106 | 10/1991 | Kasevich et al. | 606/33 |
| 5,150,717 | 9/1992 | Rosen et al. | 606/33 X |

*Primary Examiner*—Peter A. Aschenbrenner
*Attorney, Agent, or Firm*—Poms, Smith, Lande & Rose

[57] ABSTRACT

A catheter combination is described using a percutaneous transluminal transmitter for transmitting energy to a localized area. The combination includes a catheter having a hollow tubular member. A transmitter combination for partial insertion into the catheter includes a continuous central conductor terminating in a tip for receiving and transmitting a signal to the tip. A dielectric material surrounds at least a significant portion of the central conductor, and a continuous coaxial conductor surrounds the dielectric material for receiving and transmitting a signal to a point adjacent the tip to form an antenna for transmitting energy to tissue when the transmitter is placed into biologic tissue. A coating around the coaxial conductor covers the coaxial conductor. A signal generator is coupled to the central conductor and the coaxial conductor for applying a signal between the central and coaxial conductors to transmit energy from the tip of the central conductor.

26 Claims, 6 Drawing Sheets

PERCUTANEOUS TRANSLUMINAL CATHETER AND TRANSMITTER THEREFOR

FIELD OF THE INVENTION

The present invention relates in general to the field of percutaneous transluminal heat treatment of tissue and angioplasty and the utilization of dilation or balloon catheters for the treatment of tissues and vascular conditions such as vascular stenoses.

More particularly, the invention relates to an improved catheter and transmission cable for use therewith which can be effectively maneuvered through tortuous vascular pathways in order to deliver readily controllable energy outputs for treating tissue and vascular conditions, such as those treated with balloon angioplasty.

BACKGROUND OF THE INVENTION

The presence of atherosclerotic plaque on the walls of blood vessels narrows the lumen of the blood vessel and reduces the flow of blood to downstream tissues. This is a particularly serious problem when the narrowing or stenosis is located in the blood vessels which provide nutrient blood to the muscles of the heart. The presence of such coronary stenotic lesions is a major predisposing factor in both acute and chronic heart problems.

Over the last decade the medical procedure known as percutaneous transluminal coronary angioplasty (PTCA) has become widely accepted as a safe and effective method for treating vascular conditions resulting from plaque formation in the coronary arteries and, to a lesser extent, in other vascular locations. Typically, this procedure utilizes a dilation catheter having an inflatable balloon at its distal end. Using a fluoroscope and radiopaque dyes for visualization, the balloon is guided into position across the stenosis and inflated for a brief period to collapse or displace the stenotic lesion in order to open the artery and reestablish adequate blood flow. A wide variety of balloon catheter designs have evolved in recent years in order to provide the vascular physician with the ability to access lesions at previously inaccessible locations along the tortuously branched pathways of the coronary arteries. Of equal importance, balloon catheters have been developed which enable the vascular physician to re-cross a vascular lesion following an initial balloon angioplasty in the event it is necessary to reopen a particularly difficult or complicated lesion.

Although relatively uncommon in PTCA, complications do arise which may require further attention by the physician. For example, cases of acute reclosure have been noted where a blood vessel will dramatically restrict or even close completely following balloon angioplasty. Typically, such acute reclosure will result from a portion of the compressed or displaced stenotic lesion breaking free from the vascular endothelium and projecting into the blood flow decreasing blood flow and providing a possible location for blood clot development. Alternatively, muscular spasms within the arterial walls following angioplasty may constrict the blood vessel around the site of the lesion to a point that effectively shuts off blood flow.

Where available, the current procedure for dealing with such cases of acute reclosure involves recrossing the stenotic lesion with a balloon catheter and reinflating the balloon for an extended period of time. In this manner, it is sometimes possible to reattach the atherosclerotic plaque to the wall of the artery and re-establish blood flow. Alternatively, a variety of shunts and stents have been developed for achieving the same purpose with varying degrees of success.

An additional complication that may be experienced in connection with PTCA is a phenomenon known as vascular dissection. In this situation, the tissues forming the wall of the blood vessel split or tear to varying degrees, weakening or perforating the vessel. It is again preferable then to re-cross the lesion with a stent or similar apparatus in an effort to support the damaged blood vessel while facilitating fusion of the dissection. Alternatively, more invasive forms of vascular surgery may be necessary to correct these complications.

Recently, alternative methodologies for opening restricted vascular pathways have been tested utilizing lasers and microwaves to deliver various amounts of energy to the site of stenosis. In laser angioplasty a light guide is inserted along the vascular pathway to the point of the stenosis and laser energy is utilized to vaporize the plaque forming the lesion. Microwave angioplasty utilizes a very flexible transmission line which is advanced along the vascular pathway to the site of the stenosis to deliver microwave energy which heats the atherosclerotic plaque and, theoretically softens the lesion prior to dilation with a balloon catheter. Neither of these techniques has met with much success utilizing existing technology. For example, it has proven difficult to access coronary lesions because the currently available light guides and microwave antenna/transmission lines are difficult to advance along the highly branched and convoluted pathways of the coronary arteries. Additionally, even where the stenotic lesions are readily accessible with existing devices it has proven to be difficult to effectively deliver sufficient amounts of energy to open or soften the lesion without producing unacceptable damage to the surrounding vascular tissues or to the equipment.

There are also other procedures where controlled application of energy promotes treatment of various conditions. For example, in cases of cardiac arrhythmia, localized application of thermal energy to nodal areas can often promote redevelopment of proper node structure. Other situations where delivery of a hyperthermic dose may provide beneficial treatment include treatment of vascular conditions such as other coronary artery disease, ablation of atherosclerotic plaque, and in treatment of conditions in other body cavities such as uterine and vaginal conditions.

Some device implantation procedures could also benefit from application of controlled amounts of energy. A vascular stent may be positioned by inserting the stent into the subject vessel using a catheter to properly locate the stent.

Accordingly, it is an object of present invention to provide an improved transmitter, for example of the microwave type, for use in connection with the opening of vascular lesions and the subsequent treatment of vascular conditions including acute reclosure, vascular dissection, cardiac arrhythmia, other coronary artery complications, treatment of conditions in body cavities such as uterine and vaginal conditions and for insertion of devices. In conjunction with these goals it is an object of the present invention to provide a microwave antenna or transmission cable which can be readily guided along tortuous pathways in order to provide access to lesions located in areas that were previously inaccessible to microwave treatment.

It is a further object of the present invention to provide an improved percutaneous transluminal microwave antenna which is sufficiently stiff in the axial direction to be pushable yet which retains a high degree of radial flexibility to facilitate steering and advancement along tortuous vascular pathways.

It is a still further object of the present invention to provide an improved percutaneous transluminal microwave antenna that will effectively deliver controlled amounts of energy to deeply treat target tissues.

SUMMARY OF THE INVENTION

In accordance with the present invention, an improved catheter and transmitter for use therewith for transmitting energy to a localized area provides a small, flexible but pushable and manipulable combination which can accurately and reliably supply deep but controlled energy to selected locations for more effectively delivering controlled hyperthermic doses to tissue locations and to devices. The catheter and transmitter combination can be used in a number of applications, including fusion of vascular dissections, stabilization of stenotic lesions, ablation of atherosclerotic plaque, treatment of cardiac arrhythmias and other applications. The transmitter for use with the catheter transmitter combination includes a continuous central conductor terminating in a tip for receiving and transmitting a signal to the tip. A dielectric material surrounds at least a portion of the central conductor. A continuous coaxial conductor surrounds the dielectric material for receiving and transmitting a signal to a point adjacent the tip to form a transmitter for transmitting energy to tissue when the transmitter is placed in biologic tissue. In one form of the invention, the continuous coaxial conductor is formed from a thin film deposited on and surrounding the dielectric material. In another form of the invention, the continuous coaxial conductor includes conductive elements spirally overlapped first in a first direction along the dielectric material and then in a second, opposite direction over the first spirally overlapped elements. These configurations provide a transmitter which is sufficiently stiff in the axial direction to be pushable yet retaining a high degree of radial flexibility to facilitate steering and manipulation along the narrow and tortuous vascular pathways.

In a further form of the invention, a signal generator is provided to supply the signals to the central conductor and the coaxial conductor to radiate energy from the tip of the transmitter. A thermocouple provides a signal which is a measure of the energy output, which is then fed back to the signal generator to control the energy output from the transmitter. In this manner, application of the energy to the desired location can be monitored and controlled, thereby minimizing any damage to any surrounding tissue and similarly minimizing any possible damage to the transmitter material or the catheter material.

In a further form of the invention, the central conductor is hollow for passing a guide wire therethrough. The guide wire facilitates manipulation and positioning of the transmitter for optimum treatment.

The catheter used in combination with the transmitter preferably includes an inflation balloon and one or more thermocouples to monitor the energy output of the transmitter. The catheter also preferably includes a coolant fluid supply for providing a coolant solution along the transmitter structure if necessary. The transmitter may also be used to heat or set other instruments or devices.

The invention will be more clearly understood considering the following brief description of the drawings and the detailed description of the preferred embodiments.

DETAILED DESCRIPTION OF THE PREFERRED EMBODIMENTS

Figures 1, 2, 3:
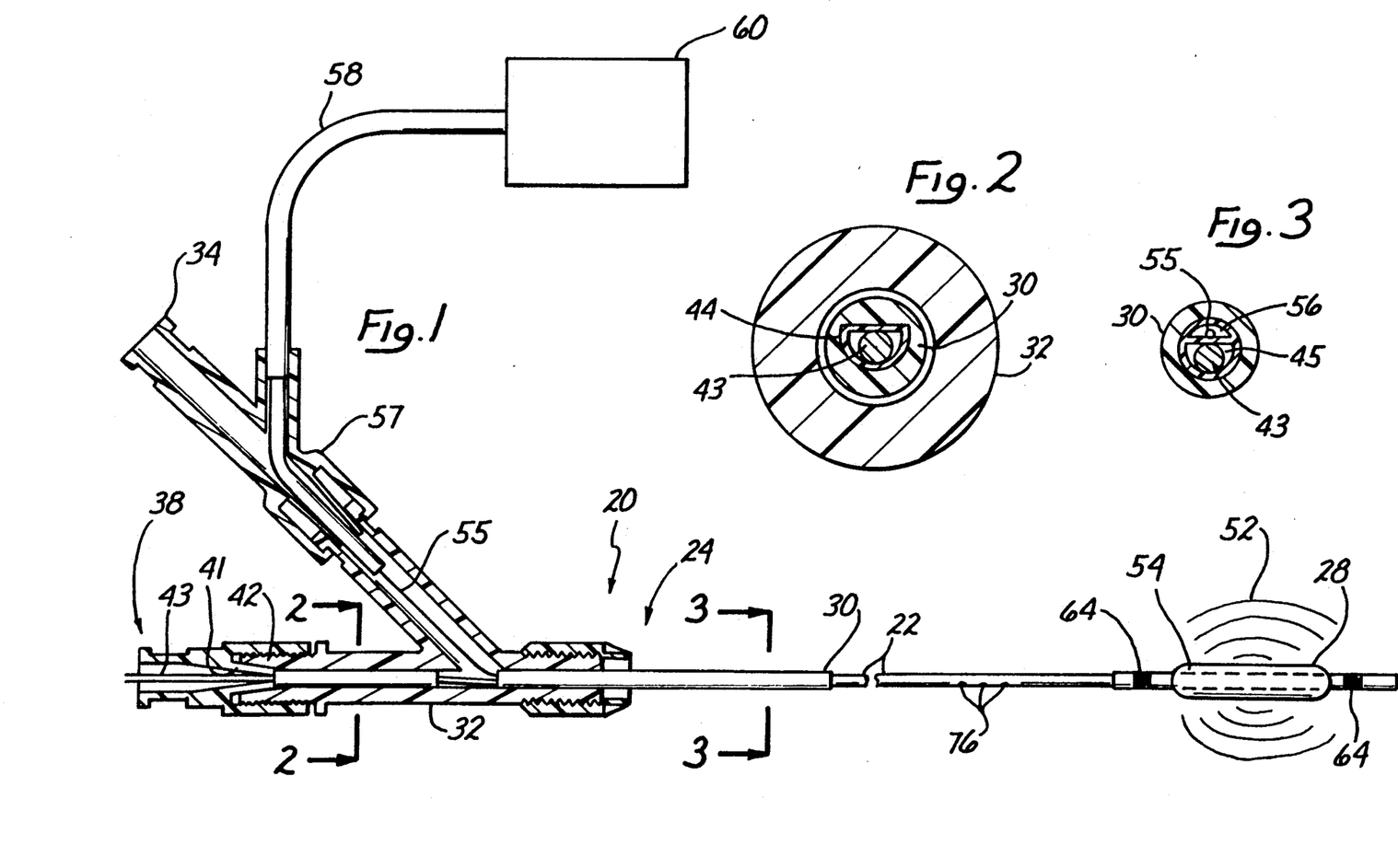
FIG. 1 is an elevation and segmented view of a catheter for use with a transmitter in the catheter and transmitter combination according to the present invention.
FIG. 2 is a transverse cross section of the Y-connector of FIG. 1 taken at 2—2 in FIG. 1.
FIG. 3 is a transverse cross section of the Y-connector of FIG. 1 taken at 3—3 in FIG. 1.

A catheter and transmitter combination for transmitting electromagnetic energy to a localized area according to the present invention provides a small, flexible and pushable combination for deep hyperthermic treatment of tissues resulting in more effective heat treatment of deep tissues than previously obtainable. The catheter 20 for use in the catheter and transmitter combination (FIG. 1) includes a flexible catheter tube 22 extending from a proximal portion 24 to a distal portion 26 in the catheter tube. Only the catheter 20 and the transmitter cable are shown in FIG. 1. The transmitter assembly is described more fully below. In the preferred embodiment, the distal portion 26 of the catheter includes an inflation balloon 28 for positioning the distal portion 26 in an artery or other body location, and for carrying out angioplasty of coronary arteries, and the like. The balloon is preferably molded concentric with the catheter tube and heat shrunk onto the outer body of the catheter tube.

The catheter is preferably a double D lumen polyolefin balloon design. The proximal end of the catheter tube 22 is protected by a strain relief 30 on a first Y-connector 32 (FIGS. 1-3). The strain relief may be a shrink wrapped tube formed around the catheter tube 22 from a point inside the first Y-connector 32 at the junction of the "Y" to a point distal of the end of the connector. The first Y-connector 32 provides access to the inflation lumen of the catheter for an inflation device coupled to an inflation port 34, as is well known to those skilled in the art. The inflation device is coupled to the first Y-connector through an adapter 36 and a second Y-connector, described more fully below.

A luer connector 38 is coupled on the main trunk of the first Y-connector 32 to accept a swivel connector 39 on the transmitter assembly 40 (FIG. 4) to minimize the creation of torque in the catheter through movement of the transmitter assembly relative to the catheter. The luer cap is threaded onto the Y-connector 32 so that a conical converging portion 41 wedges into a corresponding convergent cone section 42 on the proximal end of the Y-connector. As the luer cap threads onto the Y-connector, the convergent cone section 42 causes the converging portion 41 to form a seal around the transmitter cable 43. The transmitter cable then passes through a plastic tube 44 extending along the main portion of the Y-connector up to the "Y", where the tube terminates as shown in FIG. 1. The transmitter cable then passes into the primary lumen 45 of the catheter (FIG. 3) substantially the full length of the catheter to the balloon 28. The transmitter cable accepts signals output from the signal generator 48 (FIG. 4) through transmitter fittings 50, such as a standard SMA cable connector and transmits them radially outward from the tip of the cable and through the distal portion 26 of the catheter as depicted at 52 (FIG. 1).

In one preferred embodiment, at least one thermocouple 54 is incorporated into the inflation balloon interior to the body of the balloon for sensing the ambient temperature of the inflation fluid in the inflation balloon while electromagnetic energy is being transmitted from the cable and for feeding back a signal, representing the temperature, along thermocouple conductors 55 passed through the balloon inflation lumen 56. The thermocouple conductors are passed along the inflation lumen to a Y-connector 57 for feeding the signal back through a thermocouple cable 58 to a feedback circuit 60. The feedback circuit is associated with the signal generator 48 for forming part of a control signal for the signal generator 48, which in turn affects the output signal applied to the transmitter cable 46.

The catheter tube includes a pair of radiopaque markers 64 at the distal end 26 of the catheter 22 and positioned under the ends of the inflation balloon 28 equidistant from the center of the balloon. The markers are used to help center the end of the transmitter in the inflation balloon.

The transmitter assembly 40 (FIG. 4) is preferably a separate unit from the catheter. The transmitter assembly includes a transmitter cable 43 coupled to the SMA connector 50 in the conventional manner. A cable strain relief 66 having a base 67 bonded to the backside of the SMA connector protects the cable connection to the SMA connector and serves as a heat convection surface to carry heat away from the cable at the proximal end of the cable. The SMA connector is coupled to a reverse Y-connector 68 which houses the strain relief and connects the cable to the catheter. The branch 69 of the reverse Y-connector serves as a coupler for a coolant supply for injecting fluid into the Y-connector 68 to cool the strain relief in the reservoir 69A and the transmitter cable 43 throughout the length of the cable. The cable passes loosely through the main section of the Y-connector, through the swivel 39 and out the tube 70, which is sized so as to make a fluid-tight seal with the luer cap 38 (FIG. 1).

Figures 4, 5, 7:
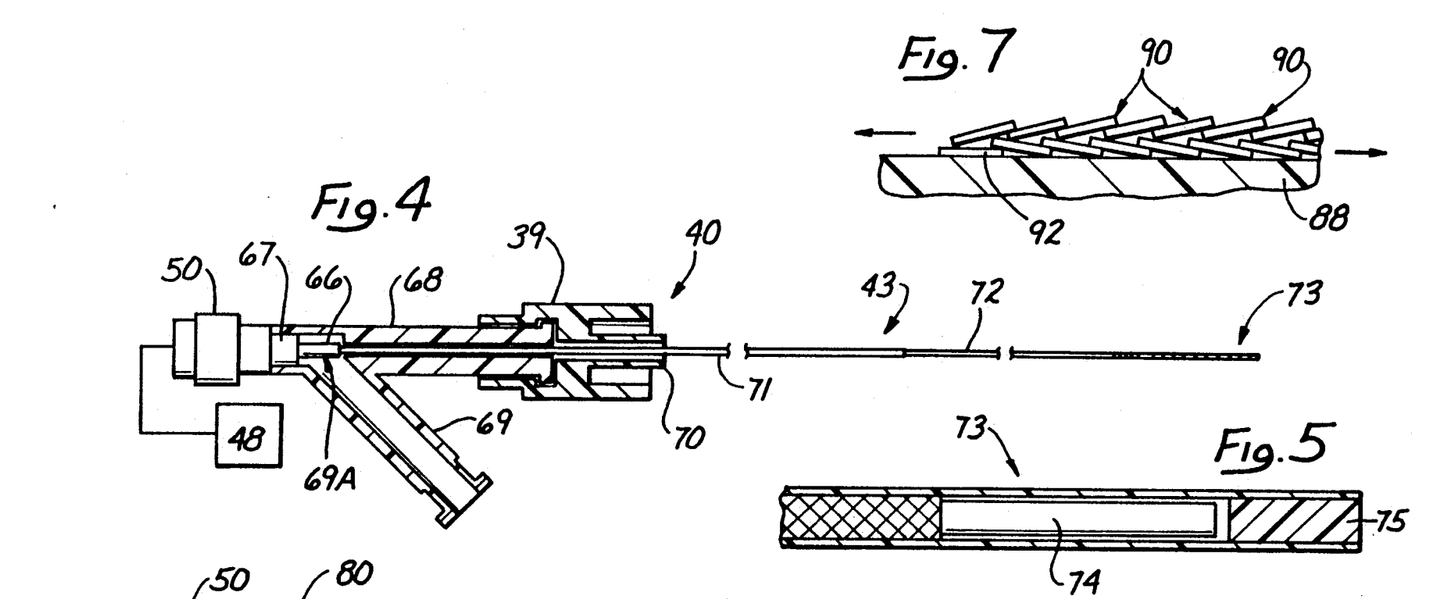
FIG. 4 is an elevation and segmented view of an electromagnetic energy transmitter with a connector having a coolant supply according to the present invention.
FIG. 5 is a segmental and expanded view of a tip of a transmitter according to the present invention.
FIG. 7 is a detailed longitudinal cross-section of a portion of the transmitter of FIG. 6 showing an overlapping arrangement of conducting elements constituting a coaxial conductor.

The cable preferably includes a proximal stiffener 71 in the form of a hypotube or a fiber or glass reinforced polyimide extending from underneath the strain relief 66 approximately four-fifths of the length of the cable. The remaining distal one-fifth of the cable is covered by a distal sheath 72 such as polyimide extending to the tip 73. The distal sheath may be a plastic insulating film or tube placed over the outer conductor beginning at the distal end of the hypotube to insulate the outer conductor and the center conductor from electronic effects such as arcing, discharge or other phenomena. The configuration of the tip 73 is shown more clearly in an exaggerated scale in FIG. 5 showing a whip form of antenna having an exposed insulator 74 around a central conductor. The detailed configuration of the cable will be described in more detail below. The distal sheath terminates in a distal plug 75 to protect the tip of the transmitter and to seal the end of the transmitter cable.

In the stainless steel hypotube, the proximal stiffener is silver soldered or otherwise attached to the coil at both ends of the hypotube. While the description of the tube 94 herein is primarily directed to a stainless steel hypotube, it should be understood that similar beneficial attributes are also achieved with other forms of tube. The hypotube enhances the pushability of the transmitter cable to allow it to be more easily pushed from the femoral artery and past the aortic arch. In one configuration where the transmitter cable, including the connector 50 is 60 inches long, the hypotube may extend approximately 47 inches beyond the end of the connector 50. In the configuration for the whip antenna, the outer conductor extends an additional 12 inches beyond the end of the hypotube, terminating approximately one inch from the tip 86. The hypotube may replace the proximal portion of the outer conductor so that the hypotube forms about four-fifths of the outer conductor, from the connector 50 out to the end of the hypotube and the beginning of the flat ribbon wire, to which the distal end of the hypotube is silver soldered.

In one preferred embodiment of the catheter of FIG. 1, the catheter tube 22 includes apertures or ports 76 formed in the wall of the catheter tube adjacent to and proximal of the inflation balloon for passing coolant injected into the primary lumen of the catheter, around the transmitter cable and through the ports to the outside of the catheter tube. There are preferably a number of ports in the wall of the catheter so as to provide a sufficient fluid flow and to distribute the fluid passing through the ports along a portion of the length of the catheter tube.

The catheter serves as a guide and carrier for the transmitter cable 43 (FIG. 1) and as one portion of the combination for carrying out the treatment of the tissue. For example, where stenotic plaque is to be tacked to a vessel wall after angioplasty, the inflation balloon 28 properly positions and maintains the location of the catheter. The transmitter cable which radiates electromagnetic energy is likewise properly positioned and held in place during the treatment by the inflation balloon. The distal thermocouple 54 continuously monitors the energy output of the transmitter cable and sends a signal representing the temperature of the surrounding tissue back to the feedback circuit 60. The preferred temperature sensed by the thermocouple 54 and which therefore is an indication of the temperature of the surrounding tissue is approximately 80 degrees Celsius. If necessary, cooling fluid may be passed into the catheter and out the ports 76 to prevent any overheating that may occur in the area of the radiating electromagnetic energy.

Figure 6:
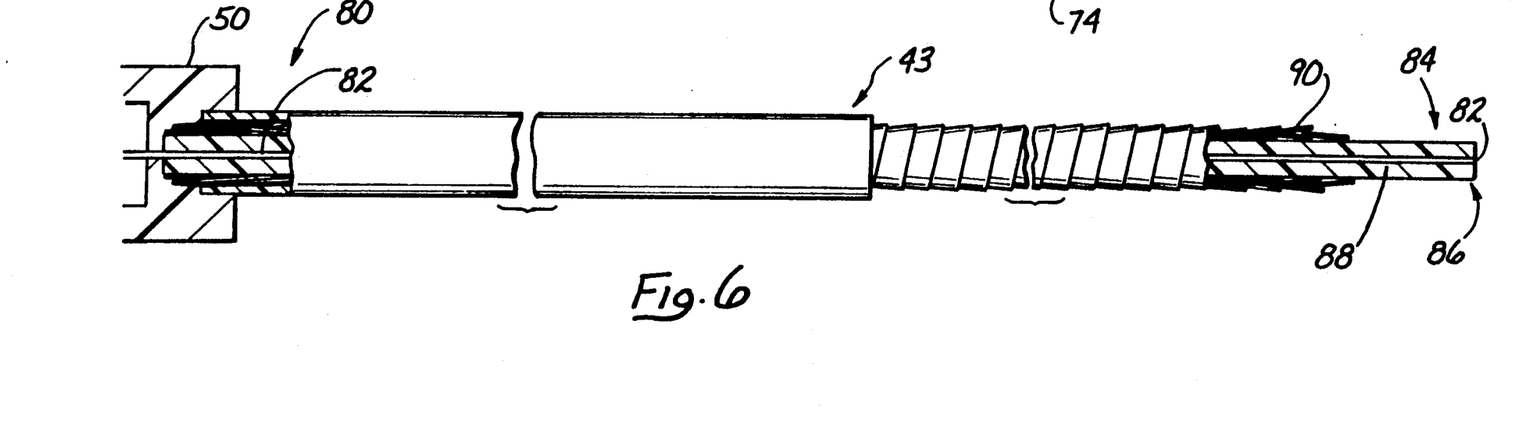
FIG. 6 is a segmented and partial cross-sectional view of a transmitter for use in the catheter and transmitter combination according to one aspect of the present invention.

The transmitter cable 43, shown in more detail in FIG. 6, includes the connector shown schematically at 50 on the proximal end 80 to connect the transmitter cable, and its several elements, to be described more fully below, to appropriate circuits in the signal generator 48. In one preferred form of the transmitter cable 43, shown in FIG. 6, the cable includes a center conductor 82 extending substantially the length of the transmitter cable from the proximal end 80 at the connector to the distal end 84. The center conductor is preferably a 0.006 inch diameter stainless steel conductor having a silver coating approximately 0.0003 inch in thickness. The center conductor not only passes the desired signal along the conductor from the connector 50 to the tip 86 of the transmitter cable, but it also provides the desired pushability for manipulating the transmitter cable through the catheter tube 22 (FIG. 1) and along the tortuous passageways along which the transmitter cable will be passed.

A dielectric material 88 surrounds the center conductor 82 preferably along the entire length of the conductor extending from the connector 50 to the tip 86 of the transmitter cable. The dielectric material 88 separates and insulates the center conductor from a second outer conductor 90. The dielectric material 88 is preferably an expanded polytetrafluoroethylene (PTFE) such as that marketed by DuPont under the trademark GORTEX. This dielectric material provides a low density insulator which can be extruded over the center conductor at a preferred outside diameter of approximately 0.017 inches, but which can be compressed down to a smaller outer diameter of approximately 0.015 inches upon application of the outer conductor 90.

The outer conductor 90 is preferably formed by two layers of right and left coiled silver-coated stainless steel ribbon conductors overlap-wound over the dielectric material 88 so as to compress the dielectric material and so as to provide a flexible outer conductor which makes the transmitter cable easier to manipulate and pass along narrow and tortuous passageways in arteries and the like. As shown most clearly in FIG. 7, the outer conductor can be considered to be overlap wound in two directions, the first or lower layer being wrapped in overlapping layers toward the right, as shown in FIG. 7, and the upper or outer layer being wrapped in overlapping layers progressing to the left, as shown in FIG. 7. FIG. 7 depicts the outer conductor overlap windings as they would be formed about the proximal end of the transmitter cable, the first winding 92 being placed flat against the dielectric material 88. Subsequent windings extending to the right over the dielectric material 88 overlap a respective immediately preceding winding and compress the dielectric material. The last winding on the lower layer also contacts the dielectric material, after which subsequent windings progressing in the opposite direction, to the left as shown in FIG. 7, overlap the respective immediately preceding winding and also cover the immediately underlying windings on the first layer. The windings on the second layer continue until the first winding 92 is reached, at which point the windings in the second layer are terminated and fixed to prevent unwinding of the outer conductor. The outer conductor 90 is preferably formed approximately 0.005 inches by 0.0015 inches. The use of this coil material for the outer conductor arranged in the described manner provides a thin, flexible and appropriately conductive outer conductor layer to form the second, coaxial conductor in the transmitter cable 43.

In the preferred embodiment, the overlapped coil of flat ribbon wire forming the second conductor terminates near the distal portion of the transmitter cable approximately one inch from the tip 86 to form a radially transmitting tip for radiating electromagnetic energy into surrounding tissue when the catheter and transmitter combination is in place. The end of the outer conductor terminating at about one inch from the cable tip 86 forms a "whip" type antenna for transmitting the energy. Alternatively, a gap type antenna can be formed by overlapping the ribbon wire all the way to the distal tip 86 of the transmitter cable and then removing a circumferential portion of the outer conductor approximately one inch proximal of the tip 86 to form a "gap" type transmitting antenna. In a further alternative, the transmitting antenna may be formed as a "helix" antenna configuration. In an alternative embodiment of the transmitter cable of FIG. 2, the outer conductor may be a single layer outer conductor.

The connector 50 is coupled to the outer conductor 90 and the center conductor 82 in the conventional manner. In this configuration, a microwave or other suitable signal can be applied to the transmitter cable and radiated from the end of the transmitter cable to provide deep hyperthermal heating of adjacent tissue.

In an alternative embodiment of the transmitter cable (FIG. 13), a center conductor 96 extends substantially the entire length of the transmitter cable from a connector 98 to the distal tip 100 of the transmitter cable. The center conductor is substantially the same as that described above with respect to FIG. 6. The center conductor is surrounded by a similar dielectric material 102 extending the length of the transmitter cable from the connector 98 to the distal tip 100. As with the transmitter cable of FIG. 6, the dielectric material may preferably be PTFE or expanded PTFE. In the present preferred embodiment of the transmitter cable, the outer conductor is formed from a gold, copper or silver, conductive film 104 formed on the outside of the dielectric material by a suitable deposition process such as sputtering or other vacuum metalization process. A preferred thickness is approximately 0.0005 inches over the outside of the dielectric material.

Figure 13:
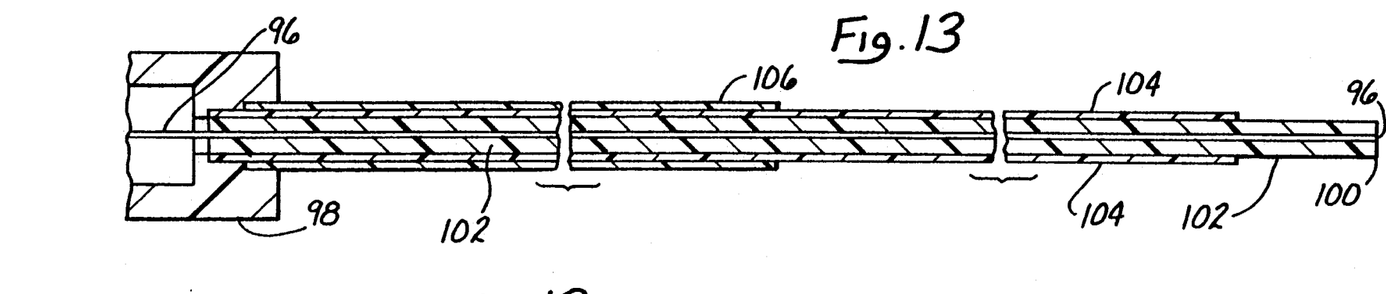
FIG. 13 is a side longitudinal section of a further embodiment of a transmitter according to the present invention wherein the second coaxial conductor is applied as a thin film, and wherein a portion of the conductor is surrounded by a hypotube.

As before, the radiating antenna portion of the transmitter cable may be formed either by omitting the last approximately one inch of outer conductor from the distal tip portion of the transmitter cable to form a whip antenna, or omitting a band of conductor material circumferentially about the transmitter cable at a discrete location proximal of the distal tip 100, to form a gap antenna. A stainless steel hypotube 106 is then placed outside the outer conductor in a manner similar to that described with respect to FIG. 2. The hypotube may be soldered at both ends to the outer conductor, or, alternatively, the hypotube may form the outer conductor for the proximal four-fifths of the length of the transmitter cable. The present embodiment using a film of conductor material formed over the outer surface of the dielectric material provides a flexible transmitter cable while still providing sufficient pushability by the thickness of the center conductor 96.

In operation, for example to treat a previously treated but collapsed stenosis, the catheter is oriented in the lumen of a cardiac artery so that the tip of the transmitter cable for radiating energy is located adjacent to stenotic plaque in the cardiac artery. The distal end of the transmitter cable is preferably located so that the transition between the end of the outer conductor and the beginning of the uncovered dielectric is centered on the lesion to be treated. The inflation balloon is preferably also centered at the center of the lesion and pressurized to apply lumen-expanding force against the plaque while the transmitting antenna radiates electromagnetic energy. A microwave signal, for example at 2450 MHz (2.45 gigaHertz) is applied to the transmitter cable at a level, and for a duration, such as for 30 seconds, sufficient to achieve treatment. The plaque is thereby heated and softened so that the plaque and the stenotic lesion can be treated as desired. Preferably, the balloon is inflated with a solution of 50 percent saline and a nonionic contrast medium and the energy applied for less than one minute, to avoid excessive heating and to avoid heating of any of the catheter combination components. The temperature at the thermocouple is preferably no greater than 80 degrees Celsius. With this design, energy transmission is maximized with a minimum of energy loss through the cable and surrounding material. If any cooling is desired, solution can be infused into the primary lumen of the catheter, out the side ports and to the outside of the catheter proximal to the inflation balloon. A suitable flow rate may be 30 milliliters per minute at 150 psi. It should be understood that electromagnetic radiation of other frequencies can also be used with the present invention.

Similar beneficial results are obtainable for other applications for the transmitter and catheter combination, or in suitable circumstances, with the transmitter in combination with other instruments. For example, in cases of cardiac arrhythmia, localized application of thermal energy to nodal areas can often promote redevelopment of proper node structure. Additionally, in treatment of vascular conditions such as coronary artery disease, vascular dissection, stabilizing stenotic lesions, ablation of atherosclerotic plaque, and in treatment of conditions in other body cavities such as uterine and vaginal conditions, controlled application of energy may be used to treat abnormal conditions. Some device implantation procedures could benefit also from application of controlled amounts of energy. A vascular stent may be positioned by inserting the stent into the subject vessel using a catheter to properly locate the stent.

The silver-coated stainless steel center conductor provides the benefit of pushability for the transmitter cable while still providing a thin profile for the transmitter cable, thereby allowing a smaller catheter and transmitter combination. Compressing the dielectric material using the flat strip conductor coil also provides a small diameter transmitter cable while still maintaining good transmission efficiency and flexibility through the dual-direction overlapped outer conductor. The thin conductor film embodiment of FIG. 4 also provides a thin transmitter cable still sufficiently flexible though pushable to traverse the tortuous passageways which often must be followed to apply suitable treatment.

In one embodiment of the method of using the catheter and transmitter cable combination described above with respect to FIGS. 1–4, the catheter can be initially positioned using a guide wire passing through the primary lumen of the catheter. After the catheter is properly positioned, the guide wire can be withdrawn and replaced with the transmitter cable, positioning the distal tip of the cable at the desired location for optimum hyperthermal treatment.

Figure 8:
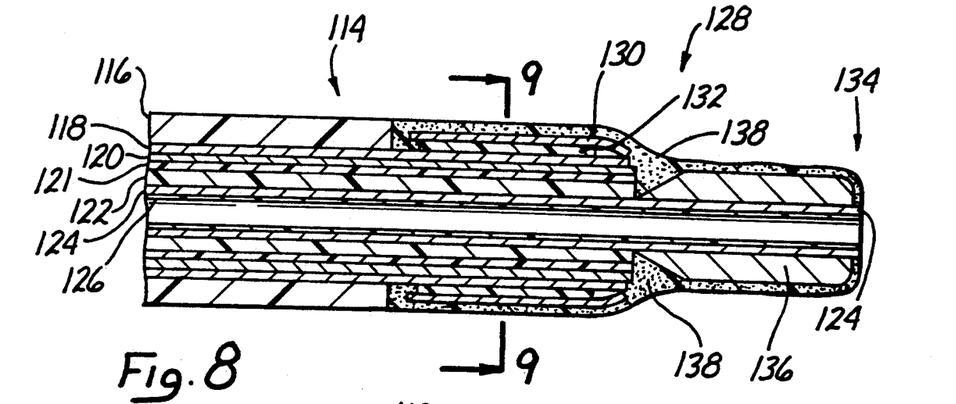
FIG. 8 shows a side longitudinal section of an end and tip portion of a transmitter according to a further aspect of the present invention forming a dipole transmitter.
Figure 9:
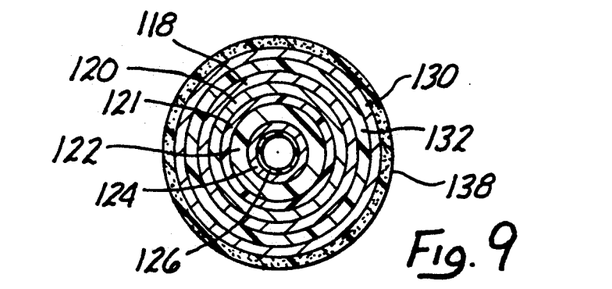
FIG. 9 is a transverse cross sectional view of a an end portion of the transmitter depicted in FIG. 8 taken along 9—9 of FIG. 8.
Figure 10:
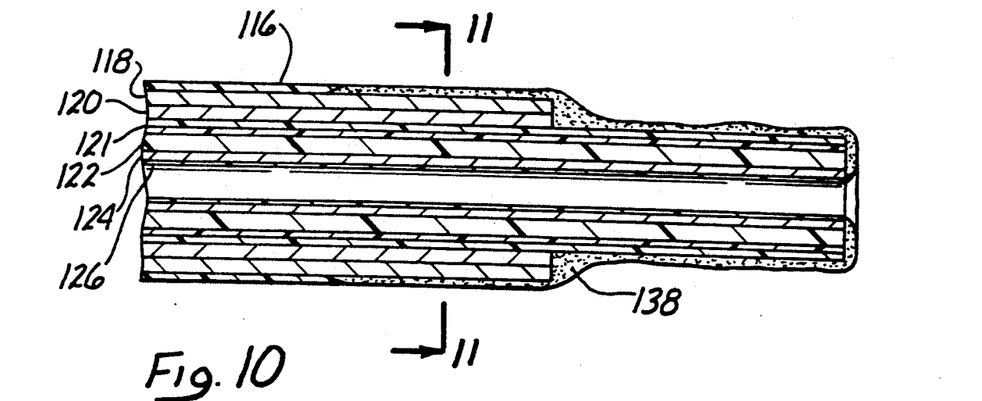
FIG. 10 shows a side longitudinal section of an end and tip portion of a transmitter according to a further aspect of the present invention forming a whip transmitter.
Figure 11:
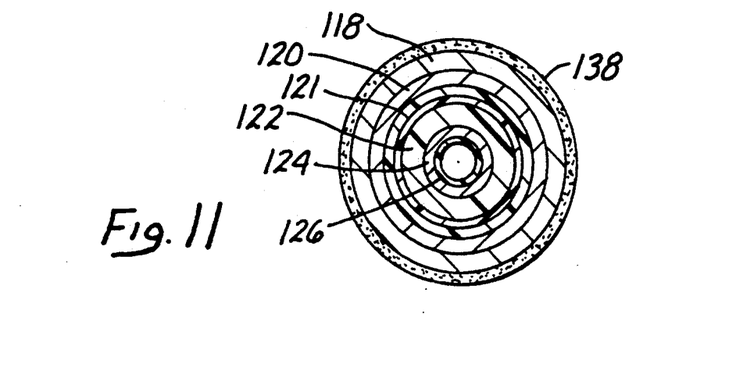
FIG. 11 is a transverse cross sectional view of a an end portion of the transmitter depicted in FIG. 10 taken along 11—11 of FIG. 10.

In a further embodiment of the transmitter according to the present invention (FIGS. 8–11), a transmitter cable 114, the distal portion of which is shown in FIG. 8, is coated with an insulation layer 116 such as Teflon PFA extending substantially the full length of the transmitter cable. The insulation protects against particulate contamination, shorting and electromagnetic radiation loss. The insulation surrounds an outer conductor which, in the embodiment shown in FIGS. 8 and 9, is formed from right and left spiraled, flat ribbon conductors, 118 and 120, respectively. The outer and inner spiral conductors preferably have the same form as those described above with respect to FIGS. 6 and 7. Alternatively, the outer conductor may be formed from conductive metal film deposited on the transmitter cable over PFA sealing layer 121 which coats a dielectric material 122. The PFA sealing layer prevents entry of any moisture or other fluid in any interstitial spaces or internally to the dielectric material 122. The sealing layer minimizes the potential for shorting, loss of signal and the like. The sealing layer is preferably about a half mil thick. The dielectric material is preferably formed from the same dielectric material as was used in the embodiment described with respect to FIGS. 6 and 7. The dielectric surrounds and insulates the central conductor 124 from the outer conductors 118 and 120. In one form of the invention, the center conductor of the transmitter cable may be formed from right and left spiraled ribbon conductors formed in much the same way as the outer conductors 118 and 120. The outer conductor layer may be a left spiral conductor while the inner conductor layer may be a right spiral conductor layer. The outer and inner spiral ribbon conductors forming the center conductor are formed so as to create a hollow passageway defined by the inside surface of the inner spiraled conductor which is then coated with a suitable insulator 126 such as Teflon, thereby forming a hollow transmitter cable for accepting a guide wire. The coatings on the central conductor also protect against shorting.

The transmitter tip may be formed in a number of configurations. For example, the outer conductor layers 116 and 118 can be removed from the distal tip, or a discontinuity can be formed therein through suitable means in the same manner as was described above with respect to FIGS. 6 and 7. Alternatively, in the case where the outer conductor is formed from a metal film, a discontinuity can be formed by masking a portion of the dielectric material before the metal film is deposited.

In one specific embodiment of the radiating portion of the transmitter conductor, a more efficient dipole transmitter can be formed by insulating a band of the outer conductor and pulling back the outer conductor from the distal tip of the transmitter cable over insulation to form the dipole transmitter, keeping the folded back ribbon conductor insulated from the underlying ribbon conductors. Specifically, the transmitter tip 128 includes a section 130 of pulled back or reversed outer conductor wrapped around an underlying layer of insulation 132 to separate the reversed conductor layer 130 from the underlying outer conductor 118. The length of the reversed conductor 130 is preferably a length phi equal to "N" times lambda divided by 4, where "N" is a positive integer. In this configuration, the outer conductor 118 and 120, the sealing layer 121 and the dielectric 122 all terminate substantially at the same point longitudinally along the transmitter cable. The inner conductor 124 and the inner insulator 126, which may be PFA or paralene, extend a further distance to the end 134 of the antenna tip. The length that the inner conductor 124 extends beyond the outer conductor is also a length phi equal to the length that the reversed conductor 130 extends. An inner antenna element 136 is welded or bonded conductively onto the outer conductor 124 to minimize the sharp transition for the inner conductor between the end of the dielectric and outer conductor and the end 134 of the transmitter. The antenna element minimizes the possibility of localized charge build-up and signal anomalies. The antenna element is preferably formed from silver or other similar element.

The dipole antenna tip is coated with an impedance matching insulating coating 138 extending from the outer insulator 116 over the distal end of the antenna element 136 and into contact with the distal-most circumferential surface of the outer conductor 124. The coating 138 is preferably formed from a varnish or resin material having a dielectric constant specifically selected to be approximately half way between the dielectric constant of saline (64) and the dielectric constant of the dielectric material, in the case of PTFE 1.15–1.2. The dielectric constant of the coating is preferably between 20 and 30. The dielectric constant of the coating is also selected to minimize the possibility of localized charge build-up and signal anomalies.

In a further embodiment of the radiating portion of the transmitter conductor (FIGS. 10 and 11), the reversed conductor is omitted and the outer conductors 118 and 120 are terminated before the sealing layer 121, the dielectric 122, the inner conductor 124 and the inner coating 126. The sealing layer, the dielectric, the inner conductor and the inner coating layer extend beyond the outer conductors a distance phi, equal to "N" times lambda divided by 4, where "N" is a positive integer and lambda is the wavelength in tissue. The impedance matching coating 138 covers the distal exposed surfaces of the inner coating, the inner conductor, the dielectric, and the sealing layer and extends proximally over the exposed ends of the outer conductors and around a relatively short length of the outer conductors to meet the coating 116.

In an alternative embodiment of the transmitter cable (not shown), the radiating portion is designed to be angularly directional. The distal tip of the dielectric material and center conductor are not fully uncovered 360° around. Specifically, the same length of the outer conductor is removed or folded back as in the previous embodiments except that only an arcuate portion is removed or folded back, leaving the rest of the outer conductor extending fully to the distal tip of the transmitter cable and covering the dielectric material.

Typical dimensions will now be discussed with respect to an exemplary 60 inch catheter. The dimensions of the catheter will vary according to the application but the dimensions of the transmitter tip will vary typically in the selection of the integer "N". In an exemplary catheter, the inside diameter of the converging luer cap is approximately 0.038 inch to allow the transmitter cable to pass through. The coolant ports 76 are approximately 0.032 inch in diameter and there are preferably three ports. The catheter may extend 0.200 inch beyond the end of the distal-most radiopaque marker 64. The outside diameter of the base 67 (FIG. 4) in one preferred embodiment may be 0.150 inch, while the outside diameter of the strain relief 66 may be 0.080 inch. The inside diameter of the branch 69 on the reverse Y-connector may be 0.165 inch, while the inside diameter of the reservoir 69A may be 0.160 inch. The inside diameter of the passageway in the reverse Y-connector through which the cable passes may be 0.100 inch. The opening at 70 may be 0.090 inch. The length of the tip 74 (FIG. 5) may be 1.5 cm. Considering the energy transmitting tip portions (FIGS. 8–11) a typical inside diameter of the hollow transmitter cable may be 0.020 inch for accepting a guide wire. A typical outside diameter of the antenna element 136 may be approximately 0.045 inch. A typical maximum outside diameter of the entire transmitter cable may be 0.065 inch. For the whip type antenna (FIGS. 10 and 11) a typical outside diameter of the seal layer may be 0.040 inch while an outside diameter of the transmitter cable may be 0.060 inch.

In one preferred embodiment of the transmitter cable, the outer conductor is preferably formed of copper having a silver coat for conductivity. A silver coat is preferred since silver oxide is still conductive whereas copper oxide is not as conductive.

This design also provides a thin, flexible but pushable transmitter cable capable of transmitting higher power density with low losses. The hollow transmitter cable allows use of a guide wire in combination with the catheter and transmitter cable combination, thereby eliminating the need for the time consuming process of replacing the guide wire in the catheter with the transmitter cable. In this embodiment, the guide wire can be used to properly position the catheter transmitter cable combination at the proper location instead of having to first locate the catheter and then insert the transmitter cable.

The uncovered length of dielectric material and center conductor which do not have an outer conductor surrounding it is typically approximately one inch in length, corresponding to one wavelength of microwave radiation transmitted in saline. As referenced above, a more efficient length is ¼ wavelength which can be achieved by folding back the outer conductor over and insulation covering the outer conductor. Overall energy density and efficiency can be optimized by making the uncovered length of the dielectric material and central conductor equal to even multiples of one quarter wavelength, i.e. "N*lambda/4", where "N" is a positive integer and lambda is the energy wavelength. Efficiency and energy density are also affected by the energy absorption at the given wavelength by the surrounding tissue, the distance from the source to the object, and the profile of the object of interest.

Figure 12:
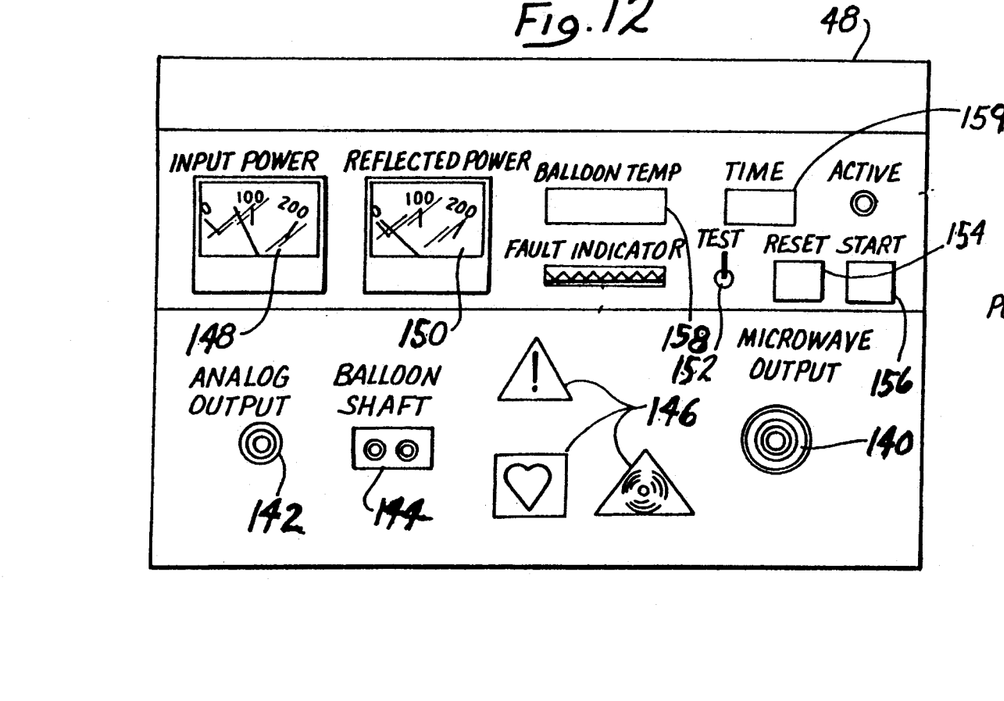
FIG. 12 is a front plan view of a signal generator for use with the present invention.

Considering generally the signal generator 48 with respect to FIG. 12, the signal generator includes a microwave output connector 140, an analogue output connector 142 and a balloon shaft thermocouple connector 144. The microwave output connector 140 ultimately connects to the connector 50 on the transmitter cable in order to apply a signal to the center conductor 82 and the outer conductor 90 to transmit and electromagnetic signal from the signal generator to the tip of the transmitter cable and to produce electromagnetic radiation to apply a thermal dose to surrounding tissue. The balloon shaft thermocouple connector 144 accepts the input from the one or more thermocouples in the catheter for monitoring the energy output for the transmitter. Various labels 146 may also be included on the front plane of the signal generator. An input power indicator 148 shows the power applied to the transmitter cable while the reflected power indicator 150 provides an indication of the transmission efficiency along the transmitter cable. Various switches including a test switch 152, a reset switch 154 and a start switch 156 are provided for operating the signal generator. A balloon temperature indicator 158 shows the detected balloon temperature represented by the signal from the distal thermocouple 54 (FIG. 1). A time indicator 159 shows the time remaining in a given cycle.

The driving and feedback circuit for the transmitter (FIGS. 14a and 14b) provides both a proper driving circuit for the transmitter and feedback of a signal representing the transmitted power level for purposes of controlling the driving signal applied to the transmitter. Specifically, power is supplied to a transformer 160 so that the secondary side of the power transformer produces an anode voltage of three kilovolts DC at 35 milliamps and a cathode filament voltage of 3.4 volts at 11.5 amps to be supplied to an electromagnetic coil, magnatron and waveguide, shown schematically at 162. The driving signal is then applied to a DC blocking capacitor 164 and then through a coupler 166 to a chassis isolating capacitor 168 and a DC blocking capacitor 170. The signal is then applied to the central and outer conductors of the transmitter placed in the catheter 20.

The signal generator detects the transmitted signal at a level of 1 watt through a crystal detector 172 and passes the signal through a series of buffers and amplifiers shown schematically at 174 to one input of a comparative amplifier 176. The other input of the comparative amplifier 176 is obtained through the crystal detectors 172 from a detected reflection signal taken at 1 watt through the coupler 166 and through a corresponding series of buffers and amplifiers 178. Analog meters 180 display the respective transmission and reflected signals detected by the crystal detectors 172. The differential amplifier 176 produces an output to a comparator 182 as a function of the voltage difference between the transmission and reflected signals on the basis of approximately 10 percent per volt. If the reflected signal is greater than 10 percent of the transmitted signal, the comparator 182 produces an output signal to the timer and control logic circuit 184 (FIG. 14a) which then produces an appropriate warning signal.

The thermocouple 54 (FIG. 14b) provides a feedback signal to a cold junction compensation circuit and buffer 186 for providing a feedback signal to the signal generator. The feedback signal is fed from the compensation circuit 186 through an isolation amplifier 188 through a buffer 190 and to a chart output device 192 on the front panel of the signal generator. The output is also provided to a comparator 194 which provides a signal to a timer 196 to determine whether or not the output power of the transmitter as determined by the thermocouple 54 has reached the proper level within a 16 second interval determined by the timer 196. If the power does not reach the proper level, a signal is provided to the timer and control logic circuit 184 to turn off the driving signal through a solid state relay circuit 198 which controls the primary side 200 of the high voltage and filament transformer for the magnatron.

Figure 14A:
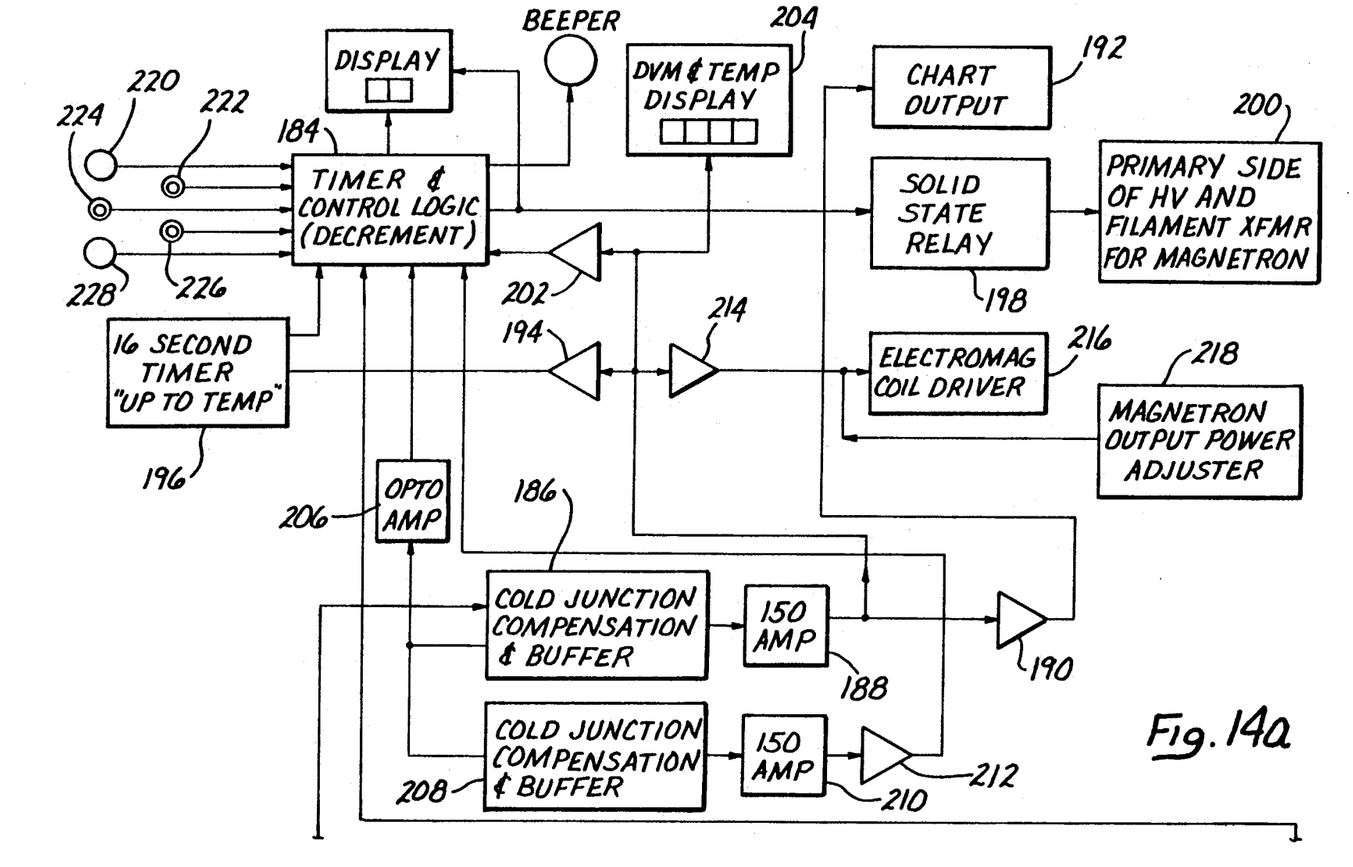
FIG. 14a and 14b are a schematic and block diagram of a transmitter driving circuit according to one aspect of the present invention.
Figure 14B:
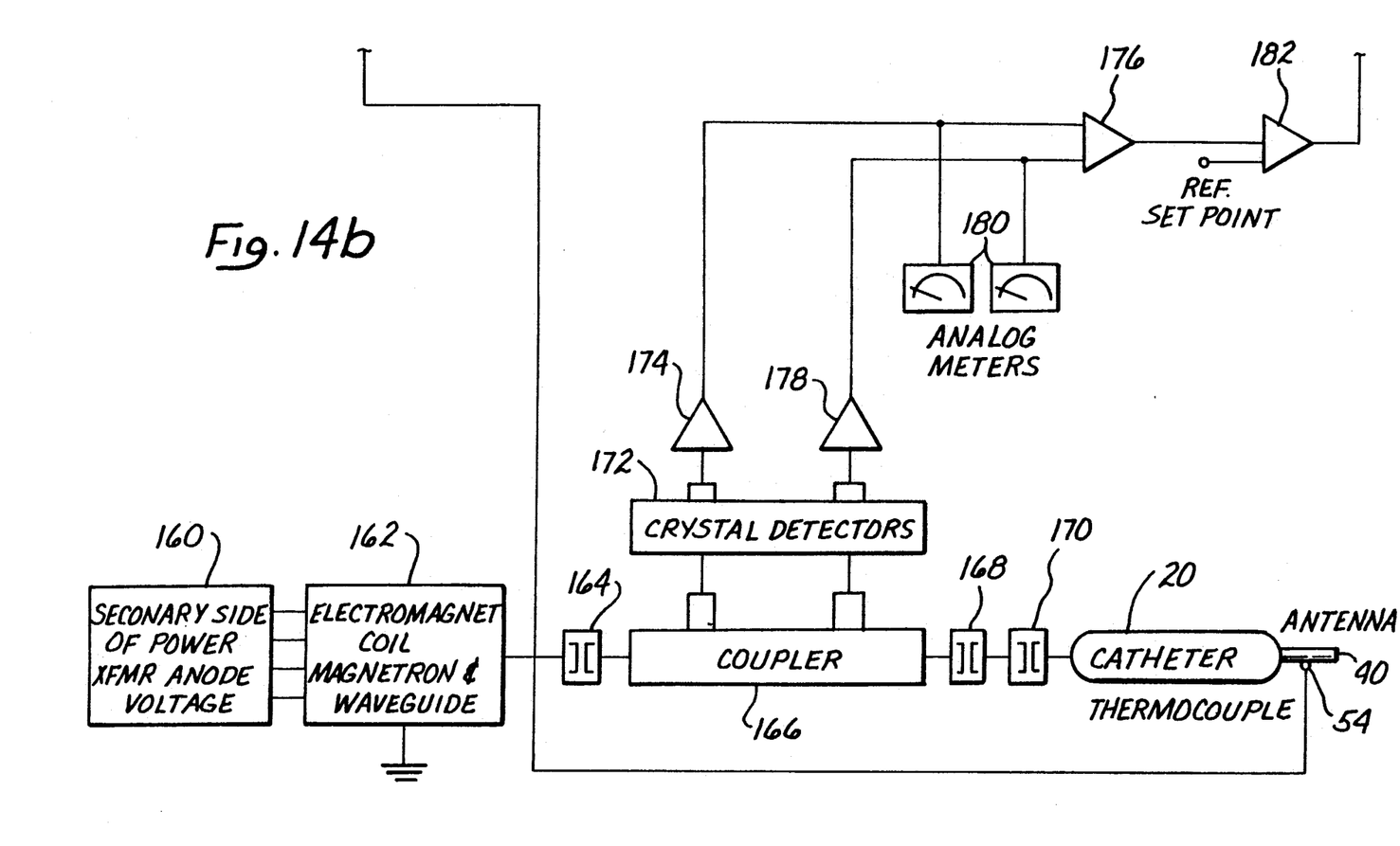

The output from the cold junction compensation circuit and buffer 186 is also applied from the isolation amplifier 188 to a comparator 202 and to a digital volt meter and temperature display 204. The comparator 202 compares the output of the thermocouple to a reference value corresponding to 95° Centigrade. If the detected temperature exceeds 95° Centigrade, a signal is provided to the timer and control logic circuit 184 to decrement the power output until the detected power is within range.

The cold junction compensation and buffer circuit 186 also provides a baseline signal to an amplifier 206 based on an open thermocouple condition. A second cold junction compensation circuit and buffer 208 may also be provided in the feedback circuit in case a second thermocouple is used. The output of the buffer 208 provides a signal to an isolation amplifier 210 providing an input to a comparator 212 which provides a signal to the timer and control logic circuit 184 if the signal from the isolation amplifier 210 represents a temperature greater than 50° Centigrade. Such a second thermocouple may, for example, be located near the proximal end of the catheter to monitor the local temperature there.

The cold junction compensation circuit and buffer 186 also provides a signal through an amplifier 214 for controlling an electromagnetic coil driver 216 which is also controlled by a magnatron output power adjustor 218. The electromagnetic coil driver is rated at 10 Ohms, 100 volts maximum at 25 watts. The typical operation is plus or minus 20 volts DC at 2.0 amps.

Various panel switches are also included to control the timer and control logic circuit 184. Switch 220 is a thumb wheel switch on an auxiliary operator's panel and switch 222 is a clear switch. Switch 224 is a start switch and switch 226 is a set switch. Switch 228 is a pendant switch.

Figure 15:
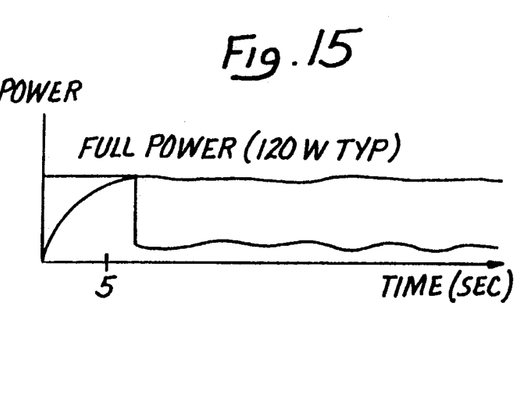
FIG. 15 is a curve representing a power versus time relationship intended to be used in conjunction with the transmitter of the present invention.

In operation, the signal generator circuit represented in FIGS. 14a and 14b provides a driving signal to the transmitter and receives feedback from the thermocouple 54 for insuring that the driving signal is maintained within acceptable boundaries. The feedback circuit turns the signal generator off if the driving signal does not reach a proper power level within the 16 second interval. The feedback circuit also turns off the signal generator if the detected temperature is greater than 95° Centigrade. As shown in FIG. 15, full power may typically be 120 watts whereas normal operating power may be around 25 watts.

Although the present invention has been described in detail with reference only to the presently preferred embodiments, it will be appreciated by those of ordinary skill in the art that various modifications can be made without departing from the spirit of the invention. Accordingly, the invention is limited only by the following claims.

We claim:

1. A catheter combination using a percutaneous transluminal transmitter for transmitting energy to a localized area, the combination comprising:
   a catheter including a hollow tubular member;
   a transmitter combination for partial insertion into the catheter including,
      a continuous central conductor terminating in a tip for receiving and transmitting a signal to the tip,
      a dielectric material surrounding at least a significant portion of the central conductor,
      a continuous coaxial conductor surrounding the dielectric material for receiving and transmitting a signal to a point adjacent the tip to form an antenna for transmitting energy to tissue when the transmitter is placed into biologic tissue, said coaxial conductor being formed in a first layer of a thin metallic ribbon wrapped in a first direction helically around said dielectric material and overlapped on itself and also in a second layer being wrapped in an opposite second direction helically around said first layer and overlapped on itself and said first layer, and
      a coating around the coaxial conductor to cover the coaxial conductor; and
   a signal generator coupled to the central conductor and the coaxial conductor for applying a signal between the central and coaxial conductors to transmit energy from the tip of the central conductor.

2. The catheter combination of claim 1 wherein the transmitter is a microwave energy transmitter.

3. The catheter combination of claim 1 further comprising a thermocouple at a distal portion of the catheter for measuring energy output from the transmitter.

4. The catheter combination of claim 3 wherein the thermocouple is coupled to the signal generator to feedback a control signal to the signal generator.

5. The catheter combination of claim 1 wherein the central and coaxial conductors form a dipole antenna.

6. The catheter combination of claim 1 wherein the central and coaxial conductors form a whip antenna.

7. The catheter combination of claim 1 wherein the central conductor is hollow and wherein the central conductor includes an interior wall defining a passageway along the length of the conductor for passing a guide wire therethrough.

8. The catheter combination of claim 7 wherein the interior wall of the central conductor is lined with an insulator material.

9. The catheter combination of claim 1 wherein the dielectric material is an expanded polytetrafluoroethylene.

10. The catheter combination of claim 1 wherein the central conductor tip is capped by an insulating material.

11. The catheter combination of claim 1 further comprising means for cooling the transmitter.

12. The catheter combination of claim 11 wherein the cooling means includes a connector for passing cooling fluid into the catheter.

13. The catheter combination of claim 11 wherein the cooling means includes a connector coupled to the catheter end for directing cooling fluid to a proximal end of the transmitter combination.

14. The catheter combination of claim 13 wherein the connector includes a Y-connector distal of the proximal end of the transmitter combination with a branch to allow coolant to be directed proximally toward the proximal end of the transmitter combination.

15. The catheter combination of claim 1 further comprising a swivel connector at a proximal end of the catheter to prevent application of torque to the catheter through rotation of the connector.

16. A percutaneous transluminal transmitter for transmitting energy to a localized area, the transmitter comprising:
   a continuous central conductor terminating in a tip for receiving and transmitting a signal to the tip;
   a dielectric material surrounding at least a significant portion of the central conductor;
   a continuous coaxial conductor surrounding the dielectric material for receiving and transmitting a signal to a point adjacent the tip to form an antenna for transmitting energy to tissue when the transmitter is placed into biologic tissue, said coaxial conductor being formed in a first layer of a thin metallic ribbon wrapped in a first direction helically around said dielectric material and overlapped on itself and also in a second layer being wrapped in an opposite second direction helically around said first layer and overlapped on itself and said first layer; and
   a waterproof coating around the central conductor to cover the central conductor.

17. A percutaneous transluminal transmitter for transmitting energy to a localized area, the transmitter comprising:
   a continuous central conductor terminating in a tip for receiving and transmitting a signal to the tip;
   a dielectric material surrounding at least a significant portion of the central conductor;
   a continuous coaxial conductor surrounding the dielectric material for receiving and transmitting a signal to a point adjacent the tip to form an antenna for transmitting energy to tissue when the transmitter is placed into biologic tissue, wherein the coaxial conductor includes conductive elements spirally overlapped first in a first direction along the dielectric material and then in a second direction over the first spirally overlapped elements; and
   a coating around the coaxial conductor to cover the coaxial conductor.

18. The catheter of claim 5 wherein said central conductor tip extends axially beyond said coaxial conductor to define a first dipole portion, and said coaxial conductor includes a second dipole portion extending axially away from said tip and disposed radially outwardly of said second layer of said coaxial conductor and insulated therefrom, said second dipole portion of said coaxial conductor connecting thereto adjacent said extension of said first dipole portion beyond said coaxial conductor.

19. A flexible and pushable percutaneous transluminal balloon catheter and microwave transmitter combination which is axially stiff but radially flexible for maneuvering through tortuous human vasculation, said combination comprising:
   a catheter including a dual-lumen elongate tubular body, said tubular body at a distal end portion thereof including an inflation balloon sealingly communicating with one of said dual lumens of said body, a temperature-responsive element disposed in said balloon to respond to local tissue temperature as indicated by the temperature of inflation fluid within said balloon, and an electrical conductor extending from said temperature-responsive element outwardly of said catheter via said one lumen, said body defining a coolant circulation port opening outwardly from the other lumen of said dual lumens proximal of said inflation balloon; and an elongate microwave transmitter receivable into said other lumen, said transmitter including a central conductor surrounded with dielectric and a coaxial conductor surrounding said dielectric, said coaxial conductor being formed in a first layer of a thin metallic ribbon wrapped in a first direction helically around said dielectric material and overlapped on itself and also in a second layer being wrapped in an opposite second direction helically around said first layer and overlapped on itself and said first layer, said microwave transmitter including a distal antenna portion.

20. The balloon catheter and microwave transmitter combination of claim 19 wherein said antenna portion includes said central conductor extending axially beyond said coaxial antenna to define a whip antenna microwave radiating portion.

21. The balloon catheter and microwave transmitter combination of claim 20 wherein said antenna portion includes said central conductor extending axially beyond a distal end of said coaxial antenna to define a first antenna dipole portion, and said coaxial conductor including a second dipole antenna portion extending in a proximal direction from said coaxial conductor distal end, said second dipole antenna portion being radially outwardly of and insulated from said coaxial conductor.

22. The balloon catheter and microwave transmitter combination of claim 21 wherein said second dipole antenna portion is formed by wrapping said thin metallic ribbon of said coaxial conductor about a layer of dielectric material disposed outwardly of said coaxial conductor and proximal of said coaxial conductor distal end.

23. The balloon catheter and microwave transmitter combination of claim 21 wherein said first dipole antenna portion further includes a sleeve-like inner antenna element of outer diameter substantially like that of said coaxial conductor.

24. The balloon catheter and microwave transmitter combination of claim 21 wherein said antenna portion further includes a layer of impedance matching dielectric insulation having a dielectric constant about midway between that of said dielectric material and saline.

25. The balloon catheter and microwave transmitter combination of claim 24 wherein said layer of dielectric insulation has a dielectric constant of between 20 and 30.

26. The balloon catheter and microwave transmitter combination of claim 19 wherein said central conductor is made of metallic ribbon spiral wrapped and overlapped with itself on a tube of insulator material.

* * * * *